United States Patent [19]

Hollister

[11] Patent Number: 5,423,765
[45] Date of Patent: Jun. 13, 1995

[54] REMOVABLE SAFETY NEEDLE SHEATH

[75] Inventor: William H. Hollister, Nelson, N.H.

[73] Assignee: Smiths Industries Medical Systems, Inc., Keene, N.H.

[21] Appl. No.: 57,778

[22] Filed: May 6, 1993

[51] Int. Cl.6 .............................................. A61M 5/32
[52] U.S. Cl. .................................... 604/192; 604/263; 128/763
[58] Field of Search ............... 604/192, 187, 263, 110; 128/763, 760, 919

[56] References Cited

U.S. PATENT DOCUMENTS

| | | | |
|---|---|---|---|
| 3,568,673 | 3/1971 | Cowley. | |
| 4,758,231 | 7/1988 | Harber et al. | |
| 4,883,469 | 11/1989 | Glazier | 604/263 X |
| 4,892,107 | 1/1990 | Haber | 128/763 |
| 4,972,843 | 11/1990 | Broden | 128/760 |
| 4,982,842 | 1/1991 | Hollister | 128/763 X |
| 5,106,380 | 4/1992 | Lobello | 604/198 |
| 5,139,489 | 8/1992 | Hollister | 604/192 |
| 5,154,285 | 10/1992 | Hollister | 206/365 |
| 5,207,653 | 5/1993 | Janjua et al. | 604/192 |

FOREIGN PATENT DOCUMENTS

| | | |
|---|---|---|
| 0055657 | 7/1982 | European Pat. Off. |
| 0443735 | 8/1991 | European Pat. Off. |
| 0457631 | 11/1991 | European Pat. Off. |
| 469736 | 2/1992 | European Pat. Off. |
| 2215612 | 9/1989 | United Kingdom. |
| 2217991 | 11/1989 | United Kingdom. |
| 2239607 | 7/1991 | United Kingdom. |

Primary Examiner—John D. Yasko
Attorney, Agent, or Firm—Pollock, Vande Sande & Priddy

[57] ABSTRACT

A safety needle device adaptable to fit over a tube holder includes a skirt that fittingly mates to the front end of the tube holder. A housing flexibly attached to the base of the safety device is pivotable to a position in alignment with the needle mated to the device so as to cover the same.

9 Claims, 3 Drawing Sheets

REMOVABLE SAFETY NEEDLE SHEATH

FIELD OF THE INVENTION

The present invention relates to hypodermic needles and more particularly a safety needle sheath that is adapted to be used with a reusable VACUTAINER holder and a non-reusable syringe.

BACKGROUND OF THE INVENTION

In Hollister U.S. Pat. No. 4,982,842, there is disclosed a safety needle container, to be used with a syringe, that protects a user from being accidentally pricked by the sharp end of a needle. In Hollister U.S. Pat. No. 5,139,489, the safety sheath disclosed in the '842 patent is taught to be mated to a VACUTAINER holder (tube holder). In Hollister U.S. Pat. No. 5,154,285, the '842 safety needle sheath is taught to rotatably mount about neck of a tube holder. The disclosures of the '842, '489 and '285 patents are hereby incorporated to this application by reference.

There is further disclosed in the '489 patent a variant of the invention in which the safety needle sheath is removable from the tube holder. However, this variant (shown in FIG. 4 of the '489 patent) requires that a specially designed safety needle sheath adapter be threadedly mated to a tube holder; and that after use, the housing be removed from the tube holder. This variant was found to be impractical due to its dimensional requirements.

SUMMARY OF THE PRESENT INVENTION

To provide ease of use, the present invention safety needle sheath has a base to which there is flexibly connected a safety sheath (housing) pivotable to enclose an exposed cannula of a two-ended needle mated to the base. To the end of the base away from the pivotable sheath is a cap, or skirt, that is fittable over a corresponding end of a tube holder. The lower edge of the cap portion of the base is notched at several places to mate with corresponding extensions integrated to the tube holder. In operation, a user fits the cap of the safety needle sheath over the appropriate end of the tube holder, and turns the cap to secure the same to the tube holder. After use, the safety sheath portion is twisted off from the tube holder and discarded. The tube holder can then be reused after sterilization. A second embodiment of the present invention adapts the removable safety sheath to a syringe.

It is an objective of the instant invention to provide a safety needle sheath to be conveniently used with a reusable tube holder.

It is another objective of the instant invention to provide a safety needle sheath adapted to be used with a syringe.

BRIEF DESCRIPTION OF THE DRAWINGS

The above-mentioned objectives and advantages of the present invention will become more apparent and the invention itself will be best understood by reference to the following description of embodiments of the present invention taken in conjunction with the accompanying drawings, wherein.

DETAILED DESCRIPTION OF THE INVENTION

Figure 1:
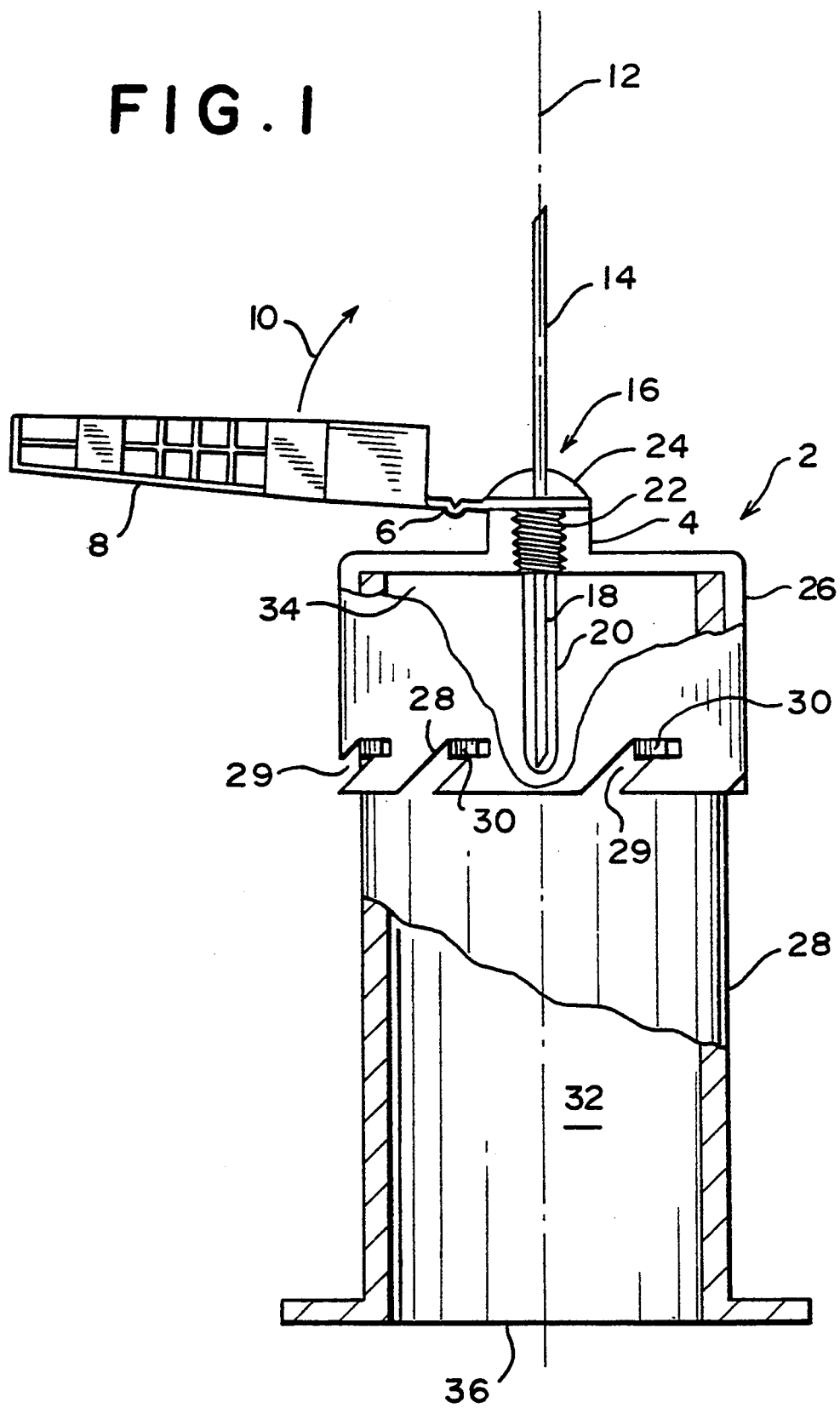
FIG. 1 is a semi-cutaway cross-sectional view of the present invention.

As shown in FIG. 1, a safety device 2 has a base 4. Connected to base 4 via a flexible connection or living hinge 6 is a sheath or housing 8, which is pivotable along the direction indicated by directional arrow 10 to be in substantial alignment along longitudinal axis 12 of cannula 14. For the FIG. 1 embodiment, cannula 14 is a first end of a double ended needle 16 whose other cannula is designated 18. Cannula 18 is enclosed by a rubber sheath 20. As shown, double ended needle 16 is threadedly mated to base 4 via its threaded portion 22 extending from its hub 24.

Extending from the lower portion of base 4 is a skirt or cap 26 whose inner circumference matches the outer circumference of a tube holder 28. Cap 26 has at its lower end a number of notches 29, configured to lockingly mate with a corresponding number of fingers 30 extending from tube holder 28. As is well known, a fluid container, such as for example a vacuum tube, can be inserted to space 32 of tube holder 28 to be in fluid communication with double ended needle 16. As shown, unlike the conventional VACUTAINER holder, tube holder 28 may be opened at both ends. Of course, it should be appreciated that end 34 of tube holder 28 may be configured to have a smaller opening than end 36, inasmuch as the size of the opening at end 34 is not that significant, so long as rubber sheath 20 can be fitted thereat. In any event, once cap 26 is fitted over tube holder 28 and is turned clockwise approximately one quarter turn so that notches 29 are lockingly secured to fingers 30, the device shown in FIG. 1 is ready for use. Further, the length of cap 26 along axis 12 extending from base 4 is sufficiently long (i.e., at least as long as cannula 18) such that the tip of cannula 18 would not be exposed when cap 26 is removed from tube holder 28.

After use, i.e., after cannula 14 has been withdrawn from the patient, sheath 8 is pivoted along directional arrow 10 to a position in substantial alignment along longitudinal axis 12 to thereby envelop cannula 14. As was disclosed in the aforenoted '842 patent, a locking mechanism, such as a number of hooks, may be formed in sheath 8 to snap onto cannula 14 to thereby fixedly retain cannula 14 within sheath 8. Thereafter, device 2 is removed from tube holder 28, by twisting cap 26 in a counterclockwise fashion so that it no longer is secured by fingers 30. Safety device 2 can then be safely disposed of. Tube holder 28, inasmuch as it is to be constructed from a sturdy polymer material, can be reused after it has been sterilized.

Figure 2:
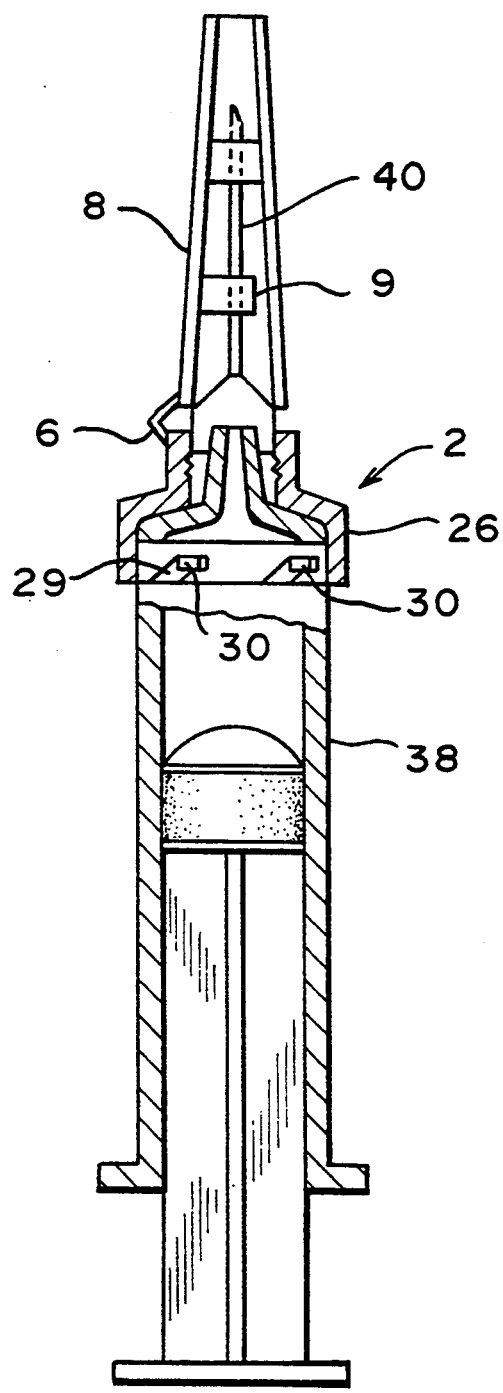
FIG. 2 is a semi-cutaway cross-sectional view of a second embodiment of the present invention.

FIG. 2 illustrates the adaptation of the safety device 2 shown in the FIG. 1 embodiment to a syringe 38. As shown, syringe 38, fitted with a needle assembly 40, is mated to a safety device 2 via its cap 26. A number of fingers 30 extending from syringe 38 secures cap 26 to syringe 38 by means of notches 29. The operation of the syringe of FIG. 2 is the same as that discussed with reference to the tube holder of FIG. 1. Thus, after use, safety device 2 is twisted off syringe 38 and disposed of. Syringe 38 is likewise disposed of.

For the FIGS. 1 and 2 embodiments, tube holder 28 and syringe 38 are special manufactured to include the respective extending fingers 30.

Figure 3:
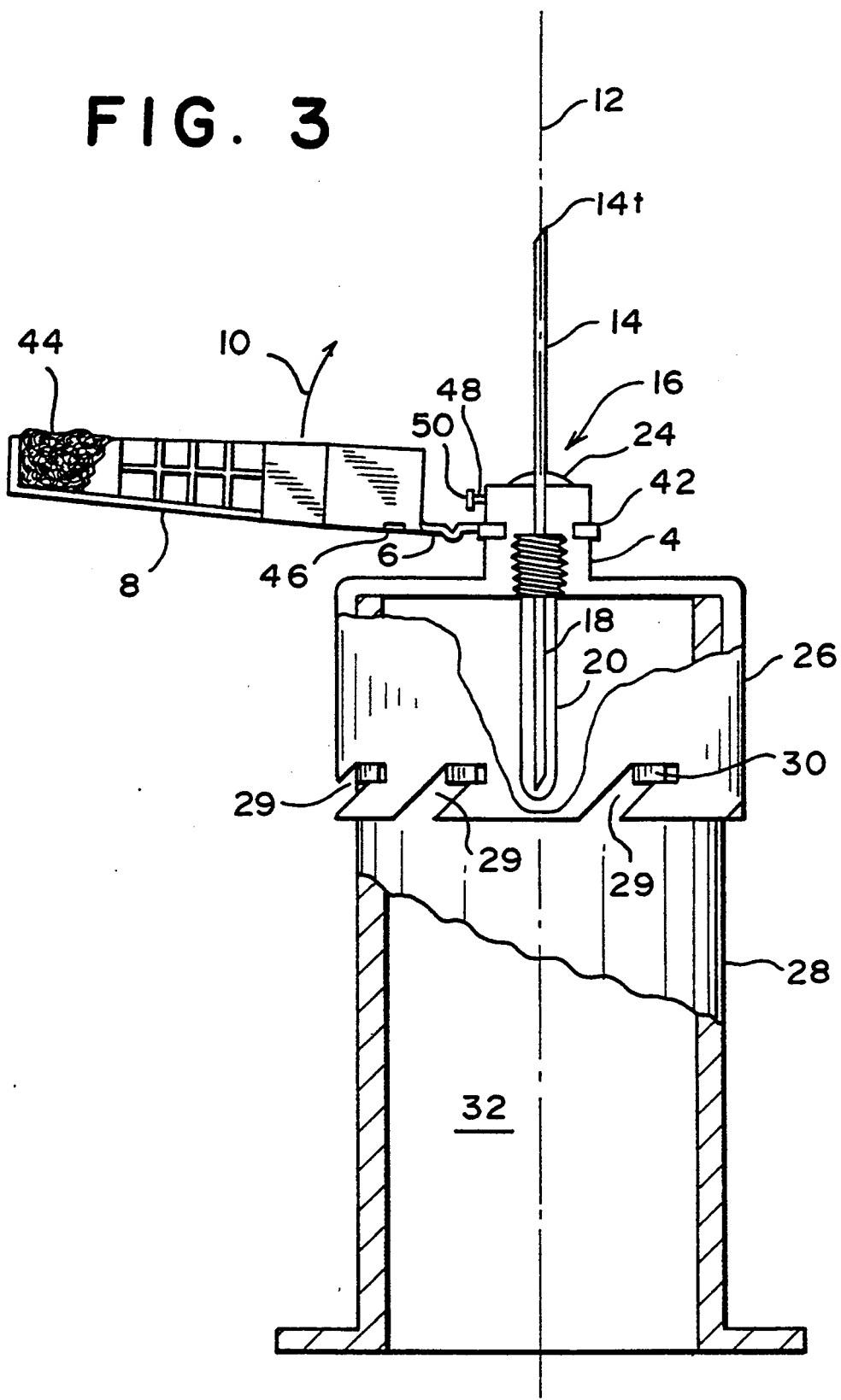
FIG. 3 is a semi-cutaway cross-sectional view of additional variations of the FIG. 1 embodiment of the instant invention.

Variants of the instant invention are shown in FIG. 3. It should be appreciated that these variants are equally applicable to the syringe embodiment shown in FIG. 2. Components in FIG. 3 which are the same as those shown in FIG. 1 are labeled the same.

As shown, the FIG. 3 embodiment illustrates the rotatable mounting of sheath 8 to base 4 by means of a non-enclosed ring 42, such as that disclosed in the '285 patent. Accordingly, sheath 8 is rotatable about base 4 so that the user can always ascertain the orientation of tip 14t of cannula 14.

A second variant of the FIG. 1 invention, as shown in FIG. 3, encompasses the inclusion of a fluid absorbable material 44 adapted to the end portion of sheath 8. Such fluid absorbable material 44 may include, for example, foam, paper, sponge or other materials that can readily absorb fluid, such as blood that may be formed at the tip of cannula 14, after it is withdrawn from a patient. Fluid absorbent material 44 is configured at sheath 8 in such a manner that it contacts cannula 14 before any hook 9 integrated within sheath 8 (see FIG. 2 and the disclosure of the '842 patent). Thus, as sheath 8 is pivoted toward axis 12, if a hook is present within sheath 8, fluid absorbable material 44 would absorb any fluid formed at tip 14t of cannula 14 before hook 9 contacts cannula 14. Thus, even were hook 9 to impart a motion to cannula 14 to cause it to shake, there is no danger of any fluid being flicked into the environment since such fluid would have been absorbed by material 44 prior to the contact between cannula 14 and hook 9. Material 44 does of course have the characteristic of readily yielding to cannula 14 as it contacts the same.

Yet another variant of the present invention uses a cooperating locking mechanism between sheath 8 and base 4 to prevent further relative movement between sheath 8 and base 4 once the former is pivoted to a position substantially in alignment along axis 12. For this variant, instead of hook 9 integrated to sheath 8, an opening 46 is provided at the lower portion of sheath 8 and an extension 48 appropriately at base 4 (assuming that sheath 8 is no longer rotatable about base 4). Extension 48 has a front end 50 that is mushroom shaped, with the tip and base portion of front end 50 being respectively configured to be smaller and larger than that of opening 46. Thus, as sheath 8 is pivoted toward the alignment position at axis 12, front end 50 would penetrate through opening 46. And after sheath 8 is positioned in alignment with axis 12, the base portion of front end 50 would prevent sheath 8 from pivoting backwards, to thereby prevent any further relative movement between sheath 8 and base 4. Other types of locking mechanisms based on cooperation between means at the base and sheath are also envisioned. For example, a plurality of openings may be formed at the sheath to cooperatively coact with and lock onto corresponding tabs formed at the base.

Inasmuch as the present invention is subject to many variation, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

I claim:

1. Safety device to be used with a holder to which a fluid container is insertable, comprising:
    a base having a first end for mating with a needle;
    a housing flexibly connected to said base pivotable to a position in substantial alignment along the longitudinal axis of said needle for enveloping said needle;
    a cap extending from a second end of said base for releasably coupling said base to a holder used with said safety device.

2. Safety device of claim 2, further comprising:
    means in said housing for retaining said needle within said housing when said housing is pivoted to said position.

3. Safety device of claim 1, wherein said cap is coupled to said holder via first latch means at said cap and corresponding second latch means at said holder.

4. Safety device of claim 2, wherein said retaining means comprises at least one hooking means integral of said housing for securely retaining said needle within said housing to prevent relative movement between said needle and said housing.

5. Safety device of claim 1, wherein said needle has a first end for insertion to a patient and a second end extending into said holder to be in fluid communication with said fluid container.

6. Safety device of claim 5, wherein said cap extends from said second end of said base to a length at least as long as said second end of said needle.

7. Safety device of claim 1, wherein said housing is rotatably mounted about said base.

8. Safety device of claim 1, further comprising:
    first latch means at said base cooperating with second latch means at said housing for preventing relative movement between said base and said housing once said housing is pivoted to said alignment position.

9. Safety device of claim 1, further comprising:
    fluid absorbing means adapted to said housing and configured to contact said needle to absorb fluid thereon before said housing is pivoted fully to said alignment position.

* * * * *